(12) United States Patent
Komuro et al.

(10) Patent No.: US 6,250,367 B1
(45) Date of Patent: Jun. 26, 2001

(54) MOLTEN METAL POURING TIMING DETERMINING APPARATUS AND CASTING MACHINE

(75) Inventors: Yoshiaki Komuro, Nishinomiya; Hidehisa Tachibana, Osaka, both of (JP)

(73) Assignee: Sansha Electric Manufacturing Company, Limited, Osaka (JP)

( * ) Notice: Subject to any disclaimer, the term of this patent is extended or adjusted under 35 U.S.C. 154(b) by 0 days.

(21) Appl. No.: 09/415,282

(22) Filed: Oct. 8, 1999

(30) Foreign Application Priority Data

Oct. 14, 1998 (JP) .................................................. 10-291801

(51) Int. Cl.⁷ .................................................. B22D 46/00
(52) U.S. Cl. .................... 164/155.6; 164/4.1; 164/457
(58) Field of Search .................... 164/4.1, 457, 155.1, 164/155.6, 150.1

(56) References Cited

U.S. PATENT DOCUMENTS

| 3,186,043 | * | 6/1965 | Murtland, Jr. et al. | ................ | 22/200 |
| 3,942,577 | * | 3/1976 | Uozumi et al. | ........................... | 164/4 |
| 5,000,046 | * | 3/1991 | Garcia et al. | ........................... | 73/597 |
| 5,633,462 | * | 5/1997 | Heaslip et al. | ........................... | 73/649 |

FOREIGN PATENT DOCUMENTS

| 62-34453 | 7/1987 | (JP) . |
| 6-85991 | 11/1994 | (JP) . |

* cited by examiner

Primary Examiner—Tom Dunn
Assistant Examiner—Len Tran
(74) Attorney, Agent, or Firm—Duane, Morris & Heckscher LLP (57) ABSTRACT

A metal material is placed in a crucible 4. An inverter 16 outputs a voltage amplitude-modulated with a low frequency signal. The output voltage is used to RF induction heat the crucible. A photodiode 30 receives light emitted by the metal material in the crucible and develops a received-light-representative signal. A high-pass filter 34 extracts, from the received-light-representative signal, a frequency component having a frequency above the frequency of the low frequency signal. A comparator 40 develops an output signal when the output signal of the high-pass filter exceeds a reference signal provided from a peak sample-and-hold circuit 42 to which the output signal of the high-pass filter is applied as an input thereto.

4 Claims, 6 Drawing Sheets

$$\frac{V_1 \times V_2}{V_3} = V_4$$

MOLTEN METAL POURING TIMING DETERMINING APPARATUS AND CASTING MACHINE

This invention relates to a casting machine for casting small articles, such as dental articles and personal ornaments, and also to an apparatus for timing the pouring of molten metal into a die of a casting machine.

BACKGROUND OF THE INVENTION

Molten metals to be cast have their own proper timings when they should be poured into a die. If molten metal is poured in a die at a time earlier than its proper pouring timing, its viscosity is too high to spread over the entire cavity in the die, so that articles cannot be cast with precision. On the other hand, if the metal is poured later than the proper pouring timing, the casting temperature is so high that the metal may be evaporated, oxidized or degraded in composition. In addition, when the metal is poured into the die, it may stick to the die because of its high temperature. Like this, the timing of pouring molten metal into the die is critical to the quality of cast articles.

Conventionally, the time at which a molten metal should be poured into a die is determined by artisans, who monitors, by eyes, the metal being melted for minute vibrations, flow, deformation, glow, color etc. of the metal, to determine when the viscosity of the entire molten metal has decreased to a viscosity suitable for pouring the metal into the die.

The proper timing of the pouring of a metal into a die is correlated to the surface temperature of the molten metal. Therefore, it has been proposed to use an infrared radiation thermometer for measuring the surface temperature of a mass of molten metal to time the pouring of the metal. It is, however, very hard to detect an accurate surface temperature of a molten metal mass with an infrared radiation thermometer because of various reasons including the following ones. First, the amount of infrared radiation emitted differs from metal to metal. In addition, for a particular metal, the surface state of the molten metal mass changes from time to time, so that the amount of infrared radiation varies from time to time, too. Furthermore, from the time at which the metal starts melting and its viscosity starts decreasing, metal films, such as an oxide film, are formed to partly cover the surface of the molten metal mass and move on the surface, which causes the amount of emission of infrared radiation detected by the thermometer to randomly vary. Also, some metals may evaporate, and the evaporated metal gas and other gas may absorb or attenuate the emitted infrared light.

Fresh metal is not always used in casting, but metal obtained by cutting off unnecessary portions of a completed cast article may be recycled. Such recycled metal has a thick oxide film on its surface, which prevents detection of correct surface temperature of the molten metal. In addition, since an infrared radiation thermometer measures the temperature only at a small point on the surface of the molten metal mass, it is not possible to know the temperature of the molten metal as a whole. In other words, it is difficult to determine when the whole molten metal attains its proper pouring temperature, with the viscosity decreased to an appropriate value.

For the reasons as above stated, when an infrared radiation thermometer is used to determine the surface temperature of molten metal, a large error may result in measured temperature, which, in turn, may result in erroneous determination of the timing of pouring of the metal into a die. Thus, an infrared radiation thermometer is not always useable to precisely time the pouring of various metals under various melting conditions.

Another possible method to determine the optimum time for pouring may be to compare the shape of a mass of metal exhibited when it is heated and melted to flow with the shape of the mass of the metal when it is solid. However, this method is not applicable to some metals and recycled metals since they have a thick or hard oxide film on their surfaces, and, therefore, the shape or appearance changes only little even when the interior has melted and liquefied enough. This may cause the metals to be heated more than necessary, leading to defective casting.

Another problem in prior art is that when a plurality of solid lumps of metal are placed in a vessel for melting, they may melt in different times and in different ways, and, therefore, it is not possible or difficult to determine when all the metal lumps have melted into a uniform molten mass only from shape or appearance changes.

Because of the problems described above, it was very difficult to realize a reliable automated casting machine which can properly operate for different melting conditions.

An object of the present invention, therefore, is to provide an apparatus for determining a proper timing of pouring molten metal and a casting machine with such pouring timing determination apparatus.

SUMMARY OF THE INVENTION

According to one aspect of the present invention, an apparatus for timing the pouring of metal into a die is provided, which includes a melting vessel for receiving a metal material therein. Heating means heats the melting vessel by RF (radio frequency) induction heating with a RF (radio frequency) signal amplitude-modulated with a low frequency signal. A light receiver receives light emitted by the metal material in the melting vessel and develops a received-light-representative signal. Frequency component extracting means extracts a frequency component having a frequency above the modulating low frequency. A comparator develops an output signal when the output of the frequency-component extracting means exceeds a reference signal.

According to the first aspect of this invention, a RF signal for RF induction heating metal in a melting vessel is amplitude-modulated with a low frequency signal. The low frequency signal may have a sinusoidal waveform. It may have any of other waveforms, such as rectangular and triangular waveforms. In melting a lump or mass of metal by RF induction heating with an induction heating current above a predetermined value, when the metal begins to melt, the molten metal mass has a spherical shape due to the electromagnetic force acting thereon. The molten metal within the spherical metal mass is stirred, so that the entire metal mass can uniformly melt. On the other hand, if the induction heating current decreases below the predetermined value, the spherical shape of the molten metal mass collapses to have a flat surface, so that it appears as if water were in a crucible. In other words, by varying the magnitude of the RF induction heating current, the shape of the mass of molten metal with a reduced viscosity can be changed. When metal starts melting and its viscosity in a surface portion starts decreasing, the shape of the molten metal mass starts changing slightly in synchronization with the low frequency signal. As the melting advances inward of the melt, the change in shape of the molten metal mass becomes larger.

As the temperature of the metal in the melting vessel rises, the amount of light emitted by the molten metal increases in proportion to the temperature. An optical detector receives the emitted light and develops a received-light-representative signal representing the amount of light received. Since the metal in the melting vessel is heated with the RF signal amplitude-modulated with the low frequency signal, the temperature of the molten metal exhibits minute changes in accordance with the low frequency signal, which results in a small change in the amount of light emitted by the molten metal. The change is extracted by the frequency component extracting means. As the metal is melted and liquefied, the shape of the molten metal mass changes largely in synchronism with the low frequency signal, which causes the distance between the optical detector and the surface of the metal mass to change. The amount of light received by the optical detector changes largely due to the effect of the combination of the variations in amount of emitted light with the variations in distance, and, therefore, the output signal of the frequency component extracting means largely varies. Such large variations are compared with the reference signal in the comparator to determine the proper timing to pour the molten metal.

A peak hold circuit may be used to hold a peak value of the output signal of the frequency component extracting means. The output signal of the peak hold circuit is used as the reference signal for the comparator.

The level of the output signal of the frequency component extracting means may change, when one or more conditions for melting metal change. Therefore, if the reference signal is fixed to a fixed value, it may occur, depending on the melting conditions, that the level of the output signal of the frequency component extracting means does not exceed the reference signal level even at the proper pouring timing. The output signal level of the frequency extracting means becomes high when the metal has melted, although the value may differ depending on the melting conditions. The level of the frequency component extracting means output signal when the metal has melted tends to be higher than the highest level developed when the metal has not yet melted. Accordingly, the peak of the output signal developed from the frequency component extracting means when the metal has not melted yet may be held in the peak hold circuit for use as the reference signal, so that the optimum timing for the pouring of the molten metal can be precisely determined.

In addition to the peak hold circuit which holds the peak value of the output signal of the frequency component extracting means, computation means may be used to multiply the ratio of the output signal of the frequency component extracting means to the output signal of the peak hold circuit by a predetermined factor. The comparator is arranged to develop an output signal when the output signal of the computation means exceeds the reference signal.

It is known that, for a particular metal, the ratio in magnitude of the output signal developed by the frequency component extracting means when the metal has not melted yet to the output signal developed when the metal has melted is substantially fixed even when one or more melting conditions change. The magnitude of the received-light representative signal from the optical detector varies when melting conditions, such as environmental conditions, the amount of metal etc. change, and it has a large value under one condition and a smaller value under other condition. Therefore, if the timing of pouring is determined based on the comparison of the output signal of the frequency component extracting means with the output of the peak hold circuit, a proper timing may not precisely be determined because of large signal variations. To improve this, the ratio of the output signal of the frequency component extracting means to the output of the peak hold circuit is multiplied by a predetermined multiplier, whereby a signal is always developed which is proportional to the ratio and varies in a given range. This signal is compared with the reference signal to determine the proper pouring time.

In stead of the peak hold circuit, a differentiating circuit may be provided to differentiate the output signal of the frequency component extracting means. The output signal of the differentiating circuit is compared with the reference signal in the comparator. The output signal developed from the comparator when the output signal from the differentiating circuit is larger than the reference signal is used as a timing signal indicating the proper pouring time. In this case, a differentiated version of the output signal developed by the frequency component extracting means when the metal starts melting may be used as the reference signal. With this arrangement, a proper pouring timing can precisely be determined even when the value of the output signal of the frequency component extracting means varies because of variable melting conditions, since melting conditions give no influence on the variation tendency of the output signal of the frequency component extracting means.

An automatic casting machine may be realized by the use of a command unit which commands that molten metal be poured from the melting vessel into a die when the comparator develops an output signal.

DETAILED DESCRIPTION OF EMBODIMENTS

Now, referring to FIGS. 1 through 4, an automated casting machine with a pouring timing determining apparatus according to a first embodiment is described. The casting machine includes a chamber 2. A casting vessel, e.g. a crucible 4, is disposed in an upper portion of the chamber 2. Within the chamber 2, below the crucible 4 is a die 6. The crucible 4 is formed of two halves having vertically extending mating surfaces. When a lump of metal 8 within the crucible 4 has melted, the lower ends of the two halves of the crucible 4 are opened, and the molten metal is poured into the die 6 through its upper pouring gate. Since the structure of the crucible 4 and the arrangement for opening the crucible 4 may be of known ones, and, therefore, they are not described in detail.

Figure 1:
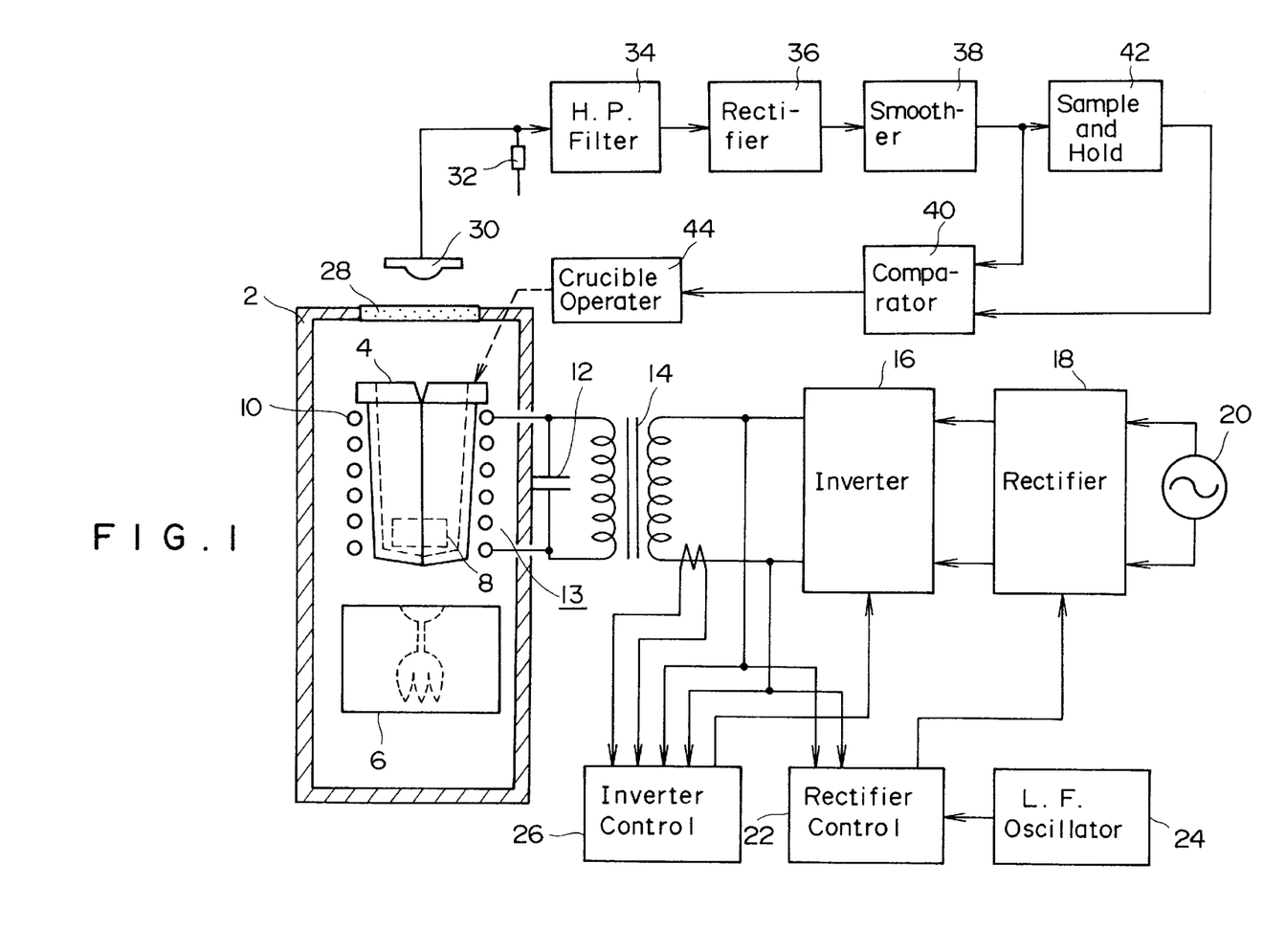
FIG. 1 is a block diagram of an automated casting machine according to a first embodiment of the present invention.

The die 6 is, for example, for casting a dental article, e.g. a false tooth, or a small personal ornament.

The crucible 4 is heated by heating means, which includes a RF induction heating coil 10 disposed on the outer surface of the crucible 4. The coil 10 is connected in parallel with a resonance capacitor 12 to form a tank circuit 13. The tank circuit 13 is connected in a secondary side of a matching transformer 14. The primary side of the matching transformer 14 is connected to the output of an inverter 16 for RF induction heating. The inverter 16 includes at least one semiconductor switching device, e.g. a thyristor, an IGBT, a power FET or a power bipolar transistor.

The input of the inverter 16 is connected to the output of a rectifying circuit 18 providing a controlled DC output voltage. The rectifying circuit 18 includes at least one semiconductor switching device, e.g. a thyristor, an IGBT, a power FET or a power bipolar transistor. The input of the rectifying circuit 18 is connected to a commercial AC power supply 20.

A rectifier control circuit 22 for controlling the rectifying circuit 18 includes a reference signal generator which generates a reference signal for use in constant voltage control. The control circuit 22 detects the output voltage of the inverter 16 and feedback controls the semiconductor switching device of the rectifying circuit 18 in such a manner as to make the output voltage of the inverter 16 have a fixed value corresponding to the reference signal.

The rectifier control circuit 22 receives from a low frequency oscillator circuit 24, a low frequency signal having a frequency of, for example, from 1 Hz to 10 Hz, or more specifically, about 2 Hz. The low frequency signal may be a sinusoidal or rectangular signal. But other signals may be used. The low frequency signal has a fixed maximum amplitude and is used as a modulating signal. The modulating signal should not have a high frequency because a high frequency modulating signal would cause little changes in shape of a mass of molten metal in the crucible 4 because of mechanical inertia of metal, and, therefore, it is hard to detect the melting of the metal. On the other hand, if the frequency of the modulating signal is too low, the temperature of the molten metal largely varies in proportion to the modulating frequency, while the changes in shape of the molten metal mass are distinct. Different appearances or shapes of the molten metal mass may result, depending also on the weight of metal to be melted, the modulating waveform, and the amplitude of the modulating low frequency signal. After various experiments, the inventors have found that the frequency of from 1 Hz to 10 Hz is desirable.

The low frequency signal, having the fixed maximum amplitude, amplitude-modulates the reference signal. Accordingly, the actual output voltage of the inverter 16 is modulated in accordance with the frequency and amplitude of the low frequency signal, and, therefore, the induction heating current flowing through the RF induction heating coil 10 is also amplitude-modulated, accordingly.

An inverter control circuit 26 is provided for the inverter 16. The inverter control circuit 26 detects the output voltage and output current of the inverter 16, and controls the switching frequency of the switching device of the inverter 16 in such a manner that the switching frequency can be equal to the resonance frequency of the tank circuit 13.

With RF induction heating used to melt metal with induction heating current having a magnitude above a predetermined value, electromagnetic force shapes the melted metal into a spherical mass. Within the spherical mass, melted metal portions are stirred, so that the metal is gradually melted into a uniform molten metal mass. If the magnitude of the induction heating current decreases below the predetermined value, the spherical shape of the molten metal mass collapses into a flat shape, i.e. it appears as if a simple liquid is within the crucible 4. Thus, the shape of the molten metal mass can be changed by adjusting the magnitude of the RF induction heating current. In order to take advantage of this characteristic, according to the present invention, the RF induction heating current is amplitude-modulated in accordance with the low frequency signal to force the current to vary about the predetermined value.

Figure 4A:
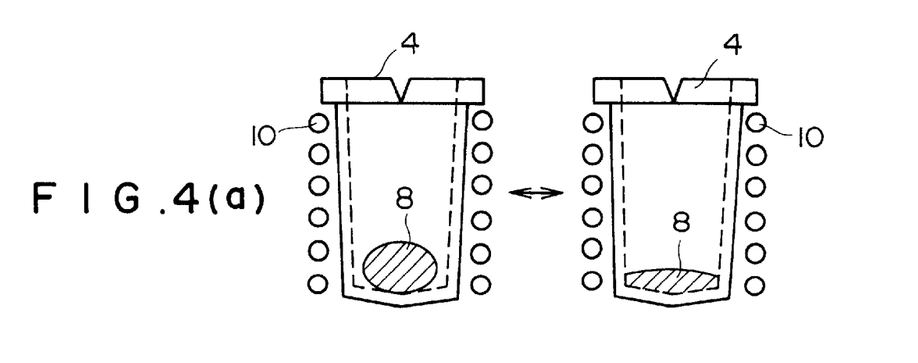
FIGS. 4(a) and 4(b) illustrate how the shape of a molten metal mass changes when the metal is melted by application of a RF signal modulated with a low frequency signal.
Figure 4B:
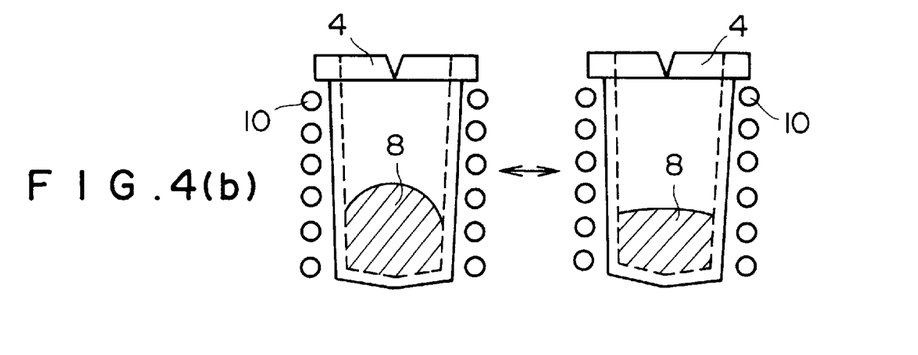

Metal does not change its appearance when it is solid. When it starts melting and the viscosity of the metal in surface portions of the metal mass decreases, the metal mass exhibits a slight change in shape in synchronization with the frequency of the low frequency signal. Before the metal has melted to the center of the mass, the change in shape of the metal mass is not large, and the appearance change occurs only in the surface portions. As the melting advances inward of the mass, the change in shape gradually increases. As shown in FIGS. 4(*a*) and 4(*b*), when the output current of the inverter 16 becomes maximum, the molten metal mass 8 becomes spherical, and when the output current is lowest, the metal mass becomes flat. FIG. 4(*a*) illustrates the shape of a relatively small mass of molten metal, and FIG. 4(*b*) does that of a relatively large mass. In each of FIGS. 4(*a*) and 4(*b*), the left side illustration shows the shape of the molten metal mass when the output of the inverter 16 is largest, and the right side illustration shows the shape of the molten metal mass when the inverter output is smallest.

In addition to the effects of RF induction heating, i.e. making the shape of the molten metal mass spherical and stirring the melt, vibrations of the molten metal caused by the forced changes in shape of the molten metal mass brought about by the amplitude-modulation of the induction heating current furthers the stirring of the molten metal in the mass so that the entire metal mass can have a uniform viscosity sooner. The time when the magnitude of change in shape of the molten metal mass exceeds a predetermined level is the proper timing for pouring the molten metal into the die 6.

Now, the pouring timing determining apparatus is described. A peephole glass plate 28 is disposed in the top portion of the chamber 2. Light emitted by the molten metal in the crucible 4 can pass through the peephole glass plate 28. A light receiver, e.g. an infrared photodiode 30 is disposed in such a manner that it can receive light emitted from various portions of the molten metal mass.

As the mass of metal 8 in the crucible 4 is heated, the amount of light, e.g. infrared light, emitted from the molten metal increases in substantial proportion to the temperature of the metal. The light emitted by the molten metal is received by the photodiode 30, which converts the received light into a received-light-representative signal, e.g. photocurrent, proportional to the amount of emitted light. The photocurrent is made to flow through a load resistor 32, in which it is converted into a voltage signal. The voltage signal is applied to frequency component extracting means, e.g. filter means, or, more specifically, a high-pass filter 34. The high-pass filter 34 allows frequency components above the frequency, e.g. about 2 Hz, of the low frequency signal from the low frequency oscillator circuit 24 to pass therethrough, but cuts off the frequency components below 2 Hz. Alternatively, a band-pass filter may be used, which allows frequency components above the frequency of 2 Hz to pass, but cuts off undesired noise in the frequency components above 2 Hz.

Figure 2:
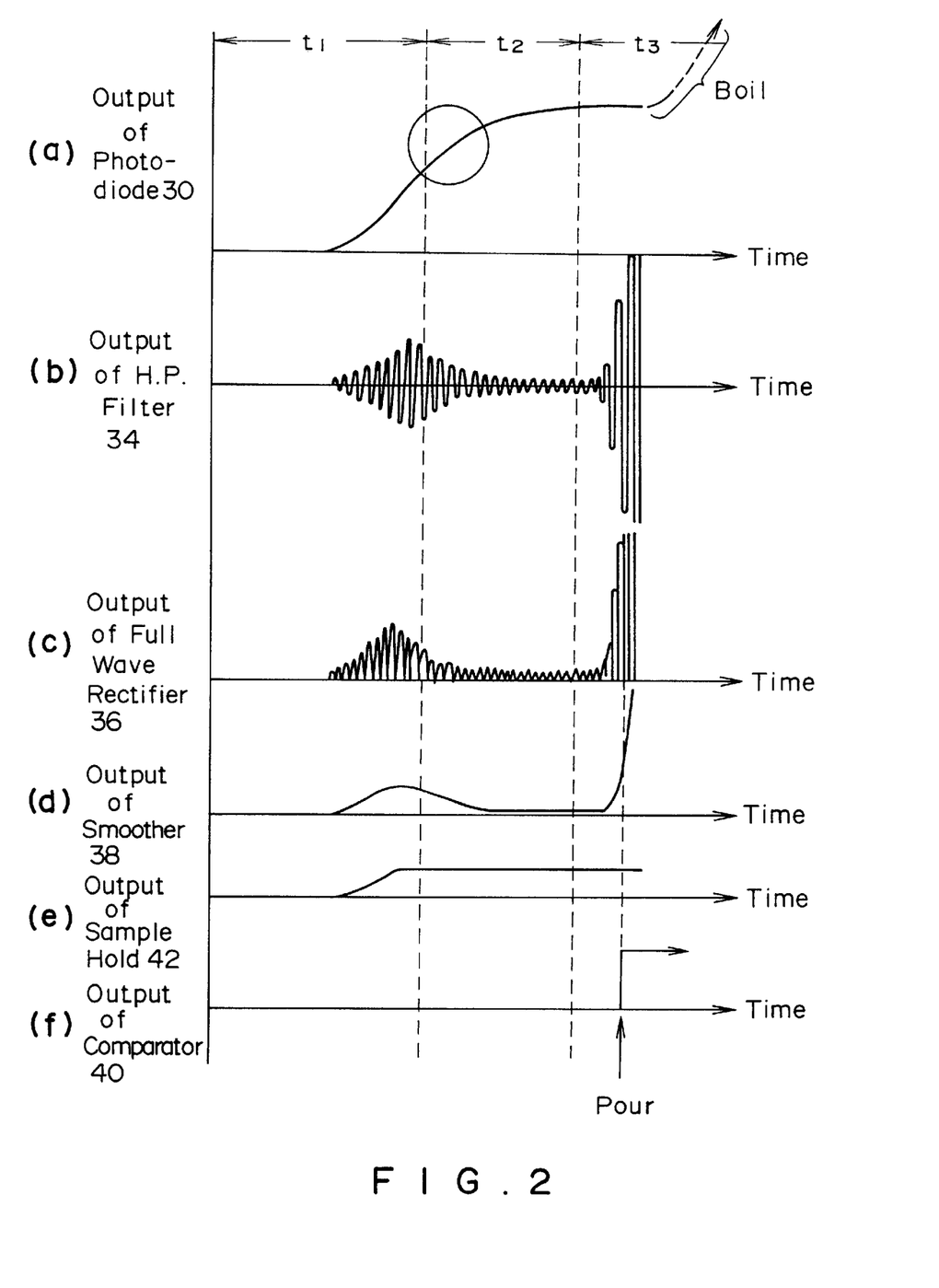
FIG. 2 shows waveforms of output signals developed at various portions of the automated casting machine shown in FIG. 1.
Figure 3:
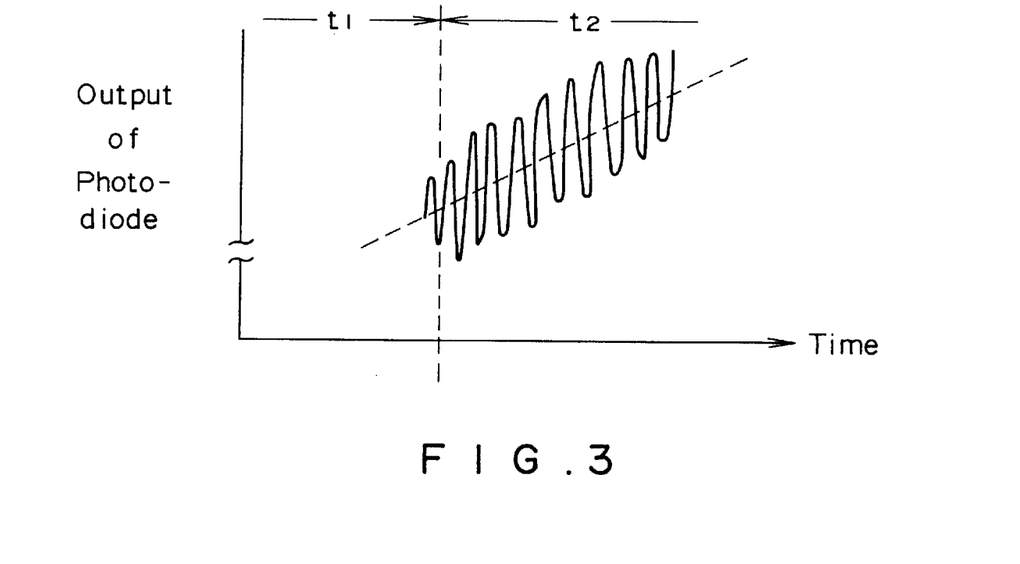
FIG. 3 shows an output waveform of a photodiode used in the automated casting machine of FIG. 1.

FIG. 2(a) shows how the photocurrent of the photodiode 30 changes with time from the beginning of the melting of the metal mass 8. The region in a circle in FIG. 2(a) is exaggeratedly shown in FIG. 3. Since the output of the inverter 16 is amplitude-modulated with the low frequency signal, the temperature of the metal mass 8 and, hence, the amount of light emitted by the molten metal mass 8 change in accordance with the change of the low frequency signal. Accordingly, as shown enlarged in FIG. 3, the photocurrent and, hence, the voltage signal developed across the load resistor 32 include an oscillating light amount component, which is synchronized with the lower frequency signal. The high-pass filter 34 extracts only this oscillating light-amount component as shown in FIG. 2(b), but removes a component corresponding to a basic temperature increase of the metal mass 8 shown in FIG. 2(a).

The temperature of the metal mass 8 rises little immediately after the beginning of the RF induction heating and, therefore, the photocurrent increases little. Then, the temperature of the metal mass 8 increases rapidly, and, therefore, the photocurrent increases rapidly, too. This time period is a heating time period indicated as period t1 in FIG. 2(a). In a time period immediately before the metal mass 8 is melted and liquefied, the rate of increase of the temperature of the metal mass 8 becomes relatively small, and, therefore, the rate of increase of the photocurrent also becomes relatively low. This period is indicated as period t2. During a period from the beginning of the melting of the metal mass 8 to the complete liquefaction, the temperature and, hence the photocurrent increase very little. This period is indicated as period t3 in FIG. 2(a). The further heating causes the temperature to rise rapidly again, which makes the photocurrent increase, too. Then, the molten metal begins to boil.

The excursion of the output signal, e.g. output voltage, of the high-pass filter 34 shown in FIG. 2(b) gradually increases to a largest excursion in the heating period t1, and gradually decreases in the period t2. In the period t3, the metal melts into liquid, and the metal mass 8 begins to change between the spherical shape and the flat shape as shown in FIG. 4(a) or 4(b) in synchronization with the frequency of the low frequency signal. This change in shape causes the distance of the surface of the molten metal mass 8 from the photodiode 30 to change. The amount of light received by the photodiode 30 changes in proportion to the square of the distance of the photodiode from the surface of the molten metal mass 8. Accordingly, the filter output exhibits a large change as is shown in the period t3 of the waveform shown in FIG. 2(b), because of the change in light amount to which the change in distance is added.

The output voltage of the high-pass filter 34 is rectified in a rectifying circuit, e.g. a full-wave rectifier circuit 36. In place of the full-wave rectifier circuit 36, a half-wave rectifier circuit may be used. The output signal, e.g. output voltage, of the full-wave rectifier circuit 36 shown in FIG. 2(c) is applied to a smoothing circuit 38, which removes pulsating components including the low frequency signal of the rectifier output voltage. This results in a mean value signal, e.g. mean value voltage like the one shown in FIG. 2(d), which is outputted from the smoothing circuit 38. The output voltage of the smoothing circuit 38 is a DC converted version of the output voltage of the high-pass filter 34 shown in FIG. 2(b).

The output voltage of the smoothing circuit 38 is compared in a comparator with a predetermined reference signal, e.g. reference voltage, for detecting the time when the output voltage of the smoothing circuit 38 abruptly increases to exceed the reference voltage. The detected time is the proper timing for pouring the molten metal into the die. More specifically, the output voltage of the smoothing circuit 38 is applied to the comparator, e.g. a voltage comparator 40 and is compared with the reference voltage. The comparator 40 is arranged to produce an output signal indicating the timing of pouring when the output voltage of the smoothing circuit 38 exceeds the reference voltage.

The reference voltage may be a predetermined, fixed voltage. The amount of light received by the photodiode 30 varies greatly in accordance with the volume of the metal in the crucible 4. The amount of received light is small when the volume of the metal is small, and the amount of light received is large when the metal volume is large. The amount of light received by the photodiode 30 is also dependent on various melting conditions including the reflection from the inner surface of the crucible 4, the position of the metal mass 8 in the crucible 4, the shape of the lump or mass of the metal, the properties and quality of the metal, the oxide film on the metal mass, the presence of gas within the crucible 4, and stains and/or flaws in the peephole glass plate. This results in change in magnitude of the output voltage of the smoothing circuit 38. Therefore, if the reference voltage of fixed value is used, there is a possibility that an improper pouring timing may be determined.

It should be noted, however, that even though any one or more of the above-described conditions change, the tendency of changes, through the time period of from t1 to t3, of the signals shown in FIG. 2 remains the same. Before the metal melts, the smoothing circuit 38 develops the output voltage of a maximum value in the vicinity of the end of the heating period t1. However, the output voltage developed by the smoothing circuit 38 when the metal has melted is always larger than this maximum value. Accordingly, in the illustrated embodiment, the reference voltage applied to the voltage comparator 40 is prepared by holding the output voltage of the smoothing circuit 38 shown in FIG. 2(d) in sample-and-hold means, e.g. a peak sample-and-hold circuit 42.

The output voltage of the peak sample-and-hold circuit 42 is shown in FIG. 2(e), which attains its maximum value in the end portion of the heating period t1 and holds the maximum value even after the metal mass 8 has melted. Accordingly, when the metal has melted, the voltage comparator 40 can develop an output signal indicating the pouring timing as shown in FIG. 2(f) under any melting conditions.

Experiments conducted for various metals under various conditions have revealed that, in general, the output voltage of the smoothing circuit 38 developed when the metal in the crucible has melted is from about two to five times as large as the output voltage of the peak sample-and-hold circuit 42.

The output signal of the voltage comparator 40 is applied to a pouring command unit, e.g. a crucible operating unit 44. In response to the voltage comparator output signal, the crucible operating unit 44 opens the crucible 4 to cause the molten metal in the crucible 4 to be poured into the die 6. In this way, the molten metal mass 8 is automatically poured into the die 6 at the most appropriate pouring time.

Figure 5:
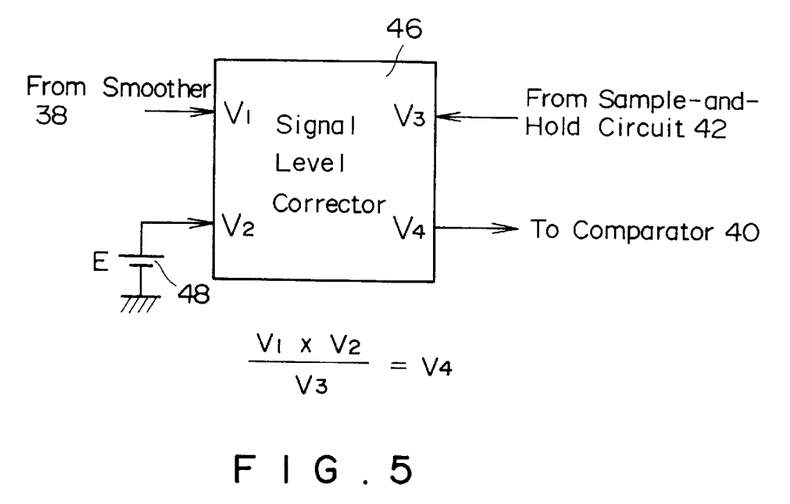
FIG. 5 is a block diagram of an automatic signal level correcting circuit used in an automated casting machine according to a second embodiment of the invention.
Figures 6A, 6C:
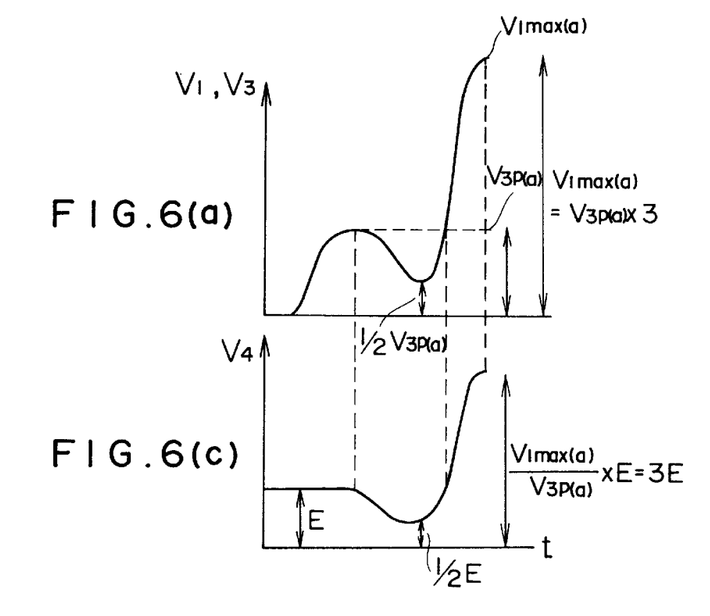
FIGS. 6(a) through 6(d) illustrate relationship between input and output signals of the automatic signal level correcting circuit of FIG. 5.
Figures 6B, 6D:
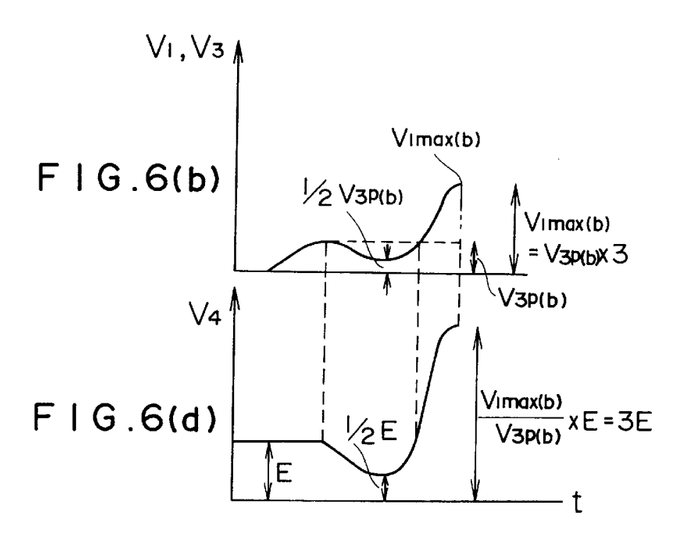
Figure 7:
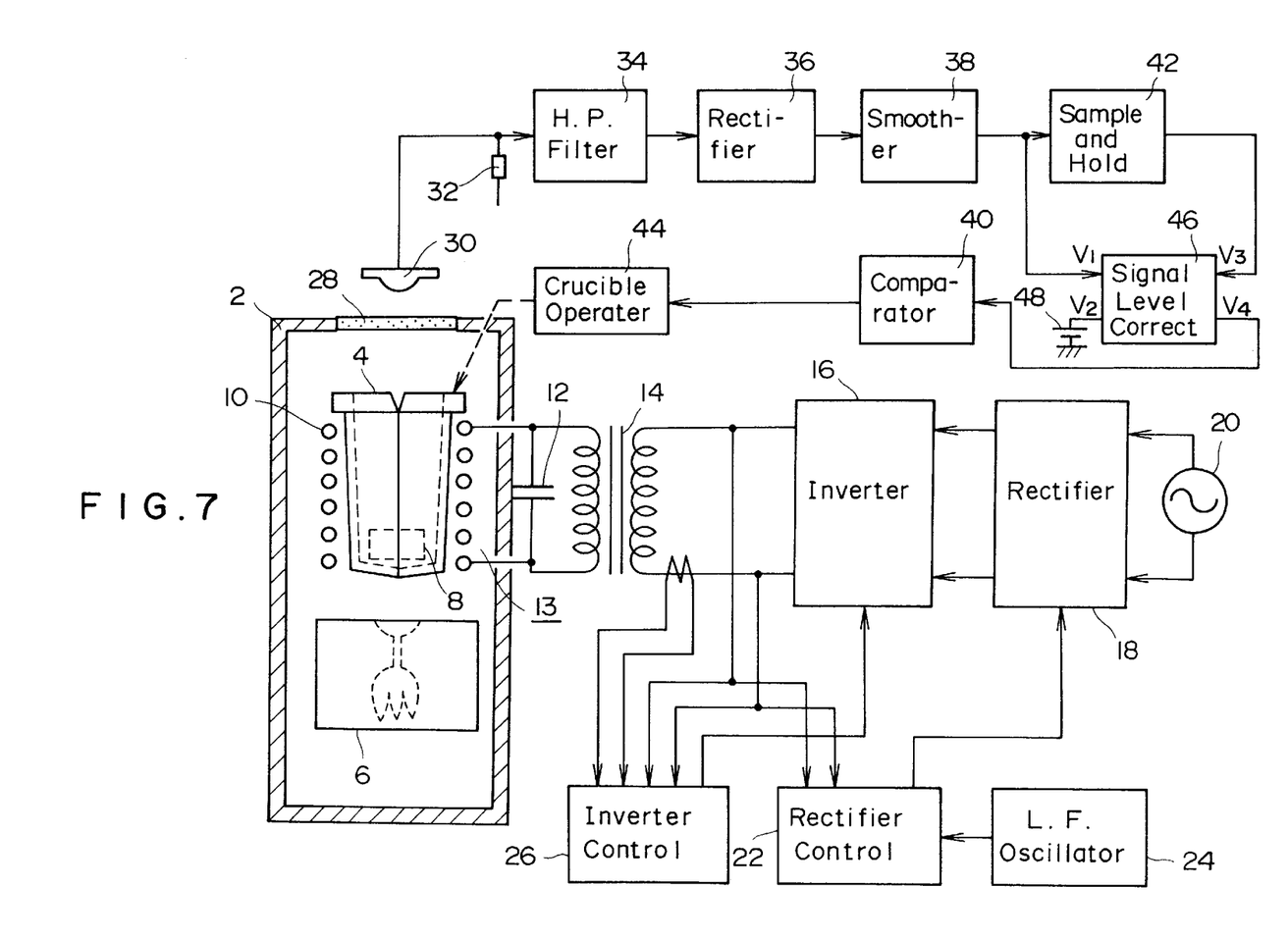
FIG. 7 is a block diagram of the automated casting machine according to the second embodiment.

FIGS. 5–7 show an automated casting machine with a pouring timing determining apparatus according to a second embodiment of the present invention. As shown in FIG. 7, the automated casting machine has the same arrangement as the automated casting machine shown in and described with reference to FIGS. 1 through 4, except that it additionally includes an automatic signal level correcting circuit 46. Therefore, the same reference numerals are used for the same components and functions, and they are not described in detail.

The automatic signal level correcting circuit 46 receives the output voltage of the smoothing circuit 38 as an input voltage V1, the output voltage from the peak sample-and-hold circuit 42 as an input voltage V3, and the reference voltage E from a reference voltage source 48 as an input voltage V2. The automatic signal level correcting circuit 46 provides an arithmetic operation of (V1/V3)*V2, and supplies, as its output voltage V4, the result of the operation to the voltage comparator 40. In other words, the automatic level correcting circuit 46 is a multiplier-divider circuit which multiplies the ratio of the output voltage of the smoothing circuit 38 to the output voltage of the peak sample-and-hold circuit 42 by a predetermined factor.

The reason that the automatic signal level correcting circuit 46 is used is as follows. The output voltage of the smoothing circuit 38 may be at a high level, as shown in FIG. 6(a), or at a lower level, as shown in FIG. 6(b), depending on various melting conditions, such as the volume of the mass of metal 8. Therefore, the direct comparison of the output voltage of the smoothing circuit 38 with the output voltage of the peak sample-and-hold circuit 42 in the voltage comparator 40 may impose a limit to the precision.

On the other hand, as previously described, even if one or more of the previously described various conditions change, the tendencies of changes through the time period of from t1 to t3 of the output voltages of the smoothing circuit 38 and the peak sample-and-hold circuit 42 are the same. Also, all signal portions of the output signals after one or more of the melting conditions have changed are increased or decreased by the same factor. That is, if the magnitude of the output voltage of the smoothing circuit 38 at the end of the time period t1 after the melting conditions have changed is two times as large as the magnitude before the change of the melting conditions, the magnitude of the output voltage at, for example, the end of the time period t2 after the change of the conditions is also two times as large as the magnitude at the corresponding time before the change of the melting conditions. The same is applicable to the output voltage of the peak sample-and-hold circuit 42. In other words, even if the conditions, such as the volume of the metal mass 8 in the crucible 4, change, the ratio of the output voltage of the smoothing circuit 38 to the output voltage of the peak sample-and-hold circuit 42 remains the same.

Accordingly, although the output voltages of the smoothing circuit 38 and the peak sample-and-hold circuit 42 may change if one or more of the melting conditions change, the ratio (V1/V3) of the output voltage (V1) of the smoothing circuit 38 to the output voltage (V3) of the peak sample-and-hold circuit 42 multiplied by the fixed voltage V2, that is, the output voltage V4 of the automatic signal level correcting circuit 46 changes in the same way, as shown in FIGS. 6(c) and 6(d).

FIG. 6(a) shows the output voltages of the smoothing circuit 38 and the peak sample-and-hold circuit 42 when they are large. FIG. 6(b) shows the output voltages of the smoothing circuit 38 and the peak sample-and-hold circuit 42 when they are small. In either case, the output voltages of the smoothing circuit 38 and the peak sample-and-hold circuit 42 are equal to each other before the output voltage of the smoothing circuit 38 attains its maximum value in the heating period t1 shown in FIG. 2(d). Accordingly, the ratio V1/V3=1, and, therefore, the output voltage V4 of the automatic signal level correcting circuit 46 is V2 (=E).

After the peak value of the output voltage of the smoothing circuit 38 is held in the peak sample-and-hold circuit 42, the output voltage of the smoothing circuit 38 gradually decreases, which results in decrease of the output voltage V4 of the automatic signal level correcting circuit 46. The rate of change of the output voltage V1 of the smoothing circuit 38 with respect to the voltage V3 held in the peak sample-and-hold circuit 42 is the same for both cases shown in FIGS. 6(a) and 6(b), and, therefore, the output voltage V4 of the automatic signal level correcting circuit 46 varies in the same fashion in both cases shown in FIGS. 6(a) and 6(b), as shown in FIGS. 6(c) and 6(d).

For example, different peak voltage values $V_{3P(a)}$ and $V_{3P(b)}$ may be held in the peak sample-and-hold circuit 42 if some conditions are different, as shown in FIGS. 6(a) and 6(b). The voltage V4 when the voltage $V_{3P(a)}$ or $V_{3P(b)}$ is held in the circuit 42 is the same, fixed voltage E. The minimum values of the output voltage V1 of the smoothing circuit 38 developed after the peak values $V_{3P(a)}$ and $V_{3P(b)}$ are held in the peak sample-and-hold circuit 42 differ. However, the ratio of the minimum value to the voltage $V_{3P(a)}$ or $V_{3P(b)}$ held in the peak sample-and-hold circuit 42 is same. Accordingly, in both cases, the value of V4 is the same as shown in FIGS. 6(c) and 6(d). In FIGS. 6(a) and 6(b), the minimum value of the output voltage V1 is exemplified as being one-half of the peak value $V_{3P(a)}$ or $V_{3P(b)}$.

Similarly, the output voltages developed when the metal has been melted may be different in the cases shown in FIGS. 6(a) and 6(b), but, since the ratio of the maximum value $V_{1max(a)}$ or $V_{1max(b)}$ of the output voltage V1 to the peak value voltage $V_{3P(a)}$ or $V_{3P(b)}$ held is the same, the value of V4 is the same both for the two cases, as shown in FIGS. 6(c) and 6(d). In the illustrated example, the maximum value $V_{1max(a)}$ or $V_{1max(b)}$ is three times as large as the peak value voltage $V_{3P(a)}$ or $V_{3P(b)}$.

The output voltage V4 of the automatic signal level correcting circuit 46 is applied to the voltage comparator 40 for comparison with an appropriate reference signal (reference voltage), e.g. the fixed voltage E. When the output voltage V4 exceeds the voltage E, the voltage comparator 40 generates an output signal, which is used as the pouring timing indicative signal. Thus, the proper pouring time can be determined with high precision even when the output levels of the smoothing circuit 38 and the peak sample-and-hold circuit 42 change due to changes of various conditions for melting metal.

The described embodiments have been described as being composed of analog signal processing circuits. However, a computer may be used. In this case, the output signal of the photodiode 30 is converted into a digital signal, and the high-pass filter 34, the full-wave rectifying circuit 36, the smoothing circuit 38, the peak sample-and-hold circuit 42, the voltage comparator 40, the crucible operating unit 44 and the automatic signal level correcting circuit 46 are formed by digital circuit technique.

Also, in place of the photodiode 30, a phototransistor may be used. Also, the photodiode 30 has been described as detecting infrared radiation emitted from the metal mass 8, a photodiode which detects visible light emitted by the metal mass 8 can be used instead.

In the described embodiments, the voltage applied to the inverter 16 is a signal which has been amplitude-controlled by a low frequency signal. Alternatively, it may be arranged that the inverter 16 may receive an ordinary DC voltage, which is then amplitude-controlled by the low frequency signal in the inverter 16 itself. In such a case, the inverter control circuit 26 controls the semiconductor switching device of the inverter 16 in such a manner that the output voltage of the inverter 16 becomes equal to the reference voltage, with the reference voltage being the sum of the DC voltage and the low frequency signal.

Figure 8:
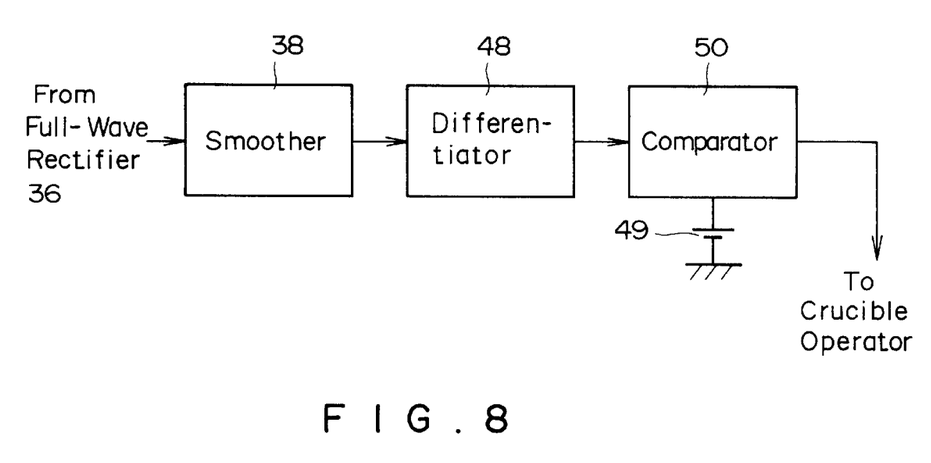
FIG. 8 is a block diagram of part of a modification of the automated casting machine according to the first embodiment of the present invention.

In place of the peak sample-and-hold circuit 42 in the first embodiment, an arrangement shown in FIG. 8 may be used. As shown in FIG. 8 the output voltage of the smoothing circuit 38 is applied to a differentiating circuit 48, and the output of the differentiating circuit 48 is compared with a reference signal provided from a reference signal source 49 in a comparator 50. When the output of the differentiating circuit 48 is larger than the reference signal, the comparator 50 develops a pouring timing indicative signal. The reference signal is the value resulting from the differentiation of the output voltage of the smoothing circuit 38 developed when the metal has been melted. In this case, too, as described previously, when one or more of the previously discussed various melting conditions change, the output voltage of the smoothing circuit 38 changes, but the change of the output voltage with time is always similar, and, therefore, the differentiation of the output voltage of the smoothing circuit 38 is always the same. Thus, a precise pouring timing can be properly determined.

What is claimed is:

1. A molten metal pouring timing determining apparatus comprising:

a melting vessel for receiving a metal material therein;

heating means for radio frequency (RF) induction heating said melting vessel with a radio frequency (RF) signal amplitude-modulated with a low frequency signal;

a light receiver for receiving light emitted by the metal material in said melting vessel and developing a light-representative signal representing the received light;

frequency component extracting means for extracting, from said light-representative signal, a frequency component having a frequency higher than said low frequency signal; and a comparator for developing an output signal when an output signal of said frequency component extracting means exceeds a reference signal; and a pouring command unit for causing molten metal in said melting vessel to be poured into a die in response to an output signal developed by said comparator.

2. The molten metal pouring timing determining apparatus according to claim 1 further comprising: a peak holding circuit for holding a peak value of the output signal of said frequency component extracting means, an output signal of said peak holding circuit being used as said reference signal.

3. The molten metal pouring timing determining apparatus according to claim 1 further comprising: a peak holding circuit for holding a peak value of the output signal of said frequency component extracting means; and computation means multiplying a ratio of the output of said frequency component extracting means to the output signal of said peak holding circuit by a predetermined factor, said comparator developing an output signal when an output signal of said computation means exceeds said reference signal.

4. A molten metal pouring timing determining apparatus comprising:

a melting vessel for receiving a metal material therein;

heating means for radio frequency (RF) induction heating said melting vessel with a radio frequency (RF) signal amplitude-modulated with a low frequency signal;

a light receiver for receiving light emitted by the metal material in said melting vessel and developing a light-representative signal representing the received light;

frequency component extracting means for extracting, from said light-representative signal, a frequency component having a frequency higher than said low frequency signal; and a comparator for developing an output signal when a differentiated version of an output signal of said frequency component extracting means exceeds a reference signal; and a pouring command unit for causing molten metal in said melting vessel to be poured into a die in response to an output signal developed by said comparator.

* * * * *